(12) United States Patent
Schott et al.

(10) Patent No.: US 11,911,493 B2
(45) Date of Patent: *Feb. 27, 2024

(54) COMPOSITIONS COMPRISING SOLVENT, A MONOALCOHOL, GLYCERIN, AND THICKENER

(71) Applicant: L'OREAL, Paris (FR)

(72) Inventors: Andrea E. Schott, New Providence, NJ (US); Aline Guimont, South Orange, NJ (US); Daniella Gonzalez-Toro, Hoboken, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/502,221

(22) Filed: Oct. 15, 2021

(65) Prior Publication Data

US 2022/0031588 A1 Feb. 3, 2022

Related U.S. Application Data

(63) Continuation of application No. 16/397,559, filed on Apr. 29, 2019, now Pat. No. 11,154,472.

(51) Int. Cl.
*A61K 8/00* (2006.01)
*A61K 8/34* (2006.01)
(Continued)

(52) U.S. Cl.
CPC ............... *A61K 8/345* (2013.01); *A61K 8/35* (2013.01); *A61K 8/8158* (2013.01); *A61Q 3/04* (2013.01);
(Continued)

(58) Field of Classification Search
CPC ......... A61K 8/345; A61K 8/8158; A61Q 3/04
See application file for complete search history.

(56) References Cited

U.S. PATENT DOCUMENTS

| 4,032,464 A | 6/1977 | Mausner |
| 4,412,027 A | 10/1983 | Klein et al. |

(Continued)

FOREIGN PATENT DOCUMENTS

| CN | 101953769 A | 1/2011 |
| CN | 105078801 A | 11/2015 |
| JP | 2014-139142 A | 7/2014 |
| TW | 201210624 A1 | 3/2012 |

OTHER PUBLICATIONS

Malhotra (Newer, Safer way to Remove Nail Polish, available online at https://www.livinghealthy.com/articles/newer-safer-way-to-remove-nail-polish, Jun. 31, 2016) (Year: 2016).

(Continued)

*Primary Examiner* — Necholus Ogden, Jr.
(74) *Attorney, Agent, or Firm* — WOMBLE BOND DICKINSON (US) LLP

(57) ABSTRACT

Compositions are provided for removing nail polish that include a co-mixture of monoalcohol, glycerin, and solvent consisting of C2-C3 monoalcohol, glycerin, and a solvent selected from acetone, a C2-C4 alkyl acetate, and combinations thereof. The composition for includes a co-mixture of monoalcohol, glycerin, and solvent that consists of C2-C3 monoalcohol; glycerin; and less than 55% by weight of solvent selected from acetone, a C2-C4 alkyl acetate, and combinations thereof. The glycerin and the C2-C3 monoalcohol are present in a glycerin to C2-C3 monoalcohol weight ratio of greater than about 0.6. If the solvent includes C2-C4 alkyl acetate then the concentration of C2-C4 alkyl acetate is less than 30% by weight. The composition further includes polyacrylamide and water. The concentration by weight of water in the composition is less than the concentration by weight of glycerin. Methods are also provided.

17 Claims, 2 Drawing Sheets

(51) Int. Cl.
  *A61K 8/35* (2006.01)
  *A61K 8/81* (2006.01)
  *A61Q 19/00* (2006.01)
  *A61Q 3/04* (2006.01)
(52) U.S. Cl.
  CPC ........ *A61Q 19/007* (2013.01); *A61K 2800/28* (2013.01); *A61K 2800/48* (2013.01); *A61K 2800/5922* (2013.01)

(56) References Cited

U.S. PATENT DOCUMENTS

| | | |
|---|---|---|
| 4,735,798 A | 4/1988 | Bernstein |
| 5,294,435 A | 3/1994 | Remz et al. |
| 5,342,536 A | 8/1994 | Miner et al. |
| 5,707,635 A * | 1/1998 | Deckner ................ A61P 37/00 424/59 |
| 6,582,684 B1 | 6/2003 | Abrahamson |
| 9,987,212 B2 | 6/2018 | MacNeill et al. |

OTHER PUBLICATIONS

L'Oreal Website (available online at https://www.lorealusa.com/csr-commitments/l%E2%80%99or%C3%A9al-answers/ the-question-of-animal-testing) (Year: 2020).

Gentle Nail Remover, Mintel GNPD, p. 1-2, Published on Aug. 2012.
Tommy Girl Sugar Scrub, Mintel GNPD, p. 1-2, Published on Nov. 2001.
Orange Nail Remover Jelly, Minetl GNPD, p. 1-3, Published on Feb. 2011.
3in1 Remover, Mintel GNPD, p. 1-2, Published on Nov. 2012.
Nail Polish Remover Gel, Mintel GNPD, p. 1-2, Published on Aug. 2007.
Nail Polish Remover Gel, Mintel GNPD, p. 1-3, Published on Jan. 2013.
Nail Polish Remover Gel, Mintel GNPD, p. 1-2, Published on Feb. 2008.
Acetone Solution Nail Polish Remover, Mintel GNPD, p. 1-3, Published on Jun. 2009.
Acetone-Based Nail Polish Remover, Mintel GNPD, p. 1-2, Published on Jul. 2005.
Orange Nail Remover Jelly, Mintel GNPD, p. 1-3, Published on Feb. 2011.
Nail Polish Remover Gel Ultra Strong, Mintel GNPD, p. 1-2, Published on May 2017.
Nail Renew (Treatment Enamel Remover), Mintel GNPD, p. 1-2, Publsihed on Nov. 2003.
Leave No Trace Glitter Nail Polish Remover, Mintel GNPD, p. 1-2, Published on Jul. 2015.

* cited by examiner

COMPOSITIONS COMPRISING SOLVENT, A MONOALCOHOL, GLYCERIN, AND THICKENER

CROSS-REFERENCE TO RELATED APPLICATIONS

The present application is based upon and claims the benefit of priority from U.S. application Ser. No. 16/397,559, filed Apr. 29, 2019, the entire contents of which are incorporated herein by reference.

FIELD OF THE INVENTION

The present invention relates to compositions and methods for removing nail polish.

DISCUSSION OF THE BACKGROUND

Nail polish compositions are typically designed to provide long-lasting color to nails. Because of the materials used in nail polish compositions to obtain the desired properties, it has proven difficult to remove such nail polish compositions from nails without adversely affecting the nails.

In particular, the inventors have recognized the need to provide efficacious nail polish removal using compositions that include highly efficacious solvents such as acetone and alkyl acetates, yet are capable of providing additional benefits such as ease of application, such as ease of application, reduced likelihood of spillage, gentle removal, and improved cosmetic experience.

SUMMARY OF THE INVENTION

The present invention relates to compositions for removing nail polish that include a co-mixture that consists of C2-C3 monoalcohol; glycerin; and less than about 55% by weight of solvent selected from acetone, a C2-C4 alkyl acetate, and combinations thereof. Within the co-mixture, the glycerin and the C2-C3 monoalcohol are present in a glycerin to C2-C3 monoalcohol weight ratio of greater than about 0.6. If the solvent includes C2-C4 alkyl acetate, then the concentration of C2-C4 alkyl acetate is less than about 30% by weight. The composition further includes polyacrylamide and water. The concentration by weight of water in the composition is less than the concentration by weight of glycerin.

The present invention also relates to methods for removing nail polish from nails and moisturizing the hands of a subject. The method includes applying a composition to the hands and to nails of a subject onto which the nail polish had been previously applied and removing the nail polish from the nails. The compositions include a co-mixture that consists of C2-C3 monoalcohol; glycerin; and less than about 55% by weight of solvent selected from acetone, a C2-C4 alkyl acetate, and combinations thereof. Within the co-mixture, the glycerin and the C2-C3 monoalcohol are present in a glycerin to C2-C3 monoalcohol weight ratio of greater than about 0.6. If the solvent includes C2-C4 alkyl acetate, then the concentration of C2-C4 alkyl acetate is less than about 30% by weight. The composition further includes polyacrylamide and water. The concentration by weight of water in the composition is less than the concentration by weight of glycerin.

It is to be understood that both the foregoing general description and the following detailed description are exemplary and explanatory only, and are not restrictive of the invention.

DETAILED DESCRIPTION OF THE INVENTION

Figure 1:
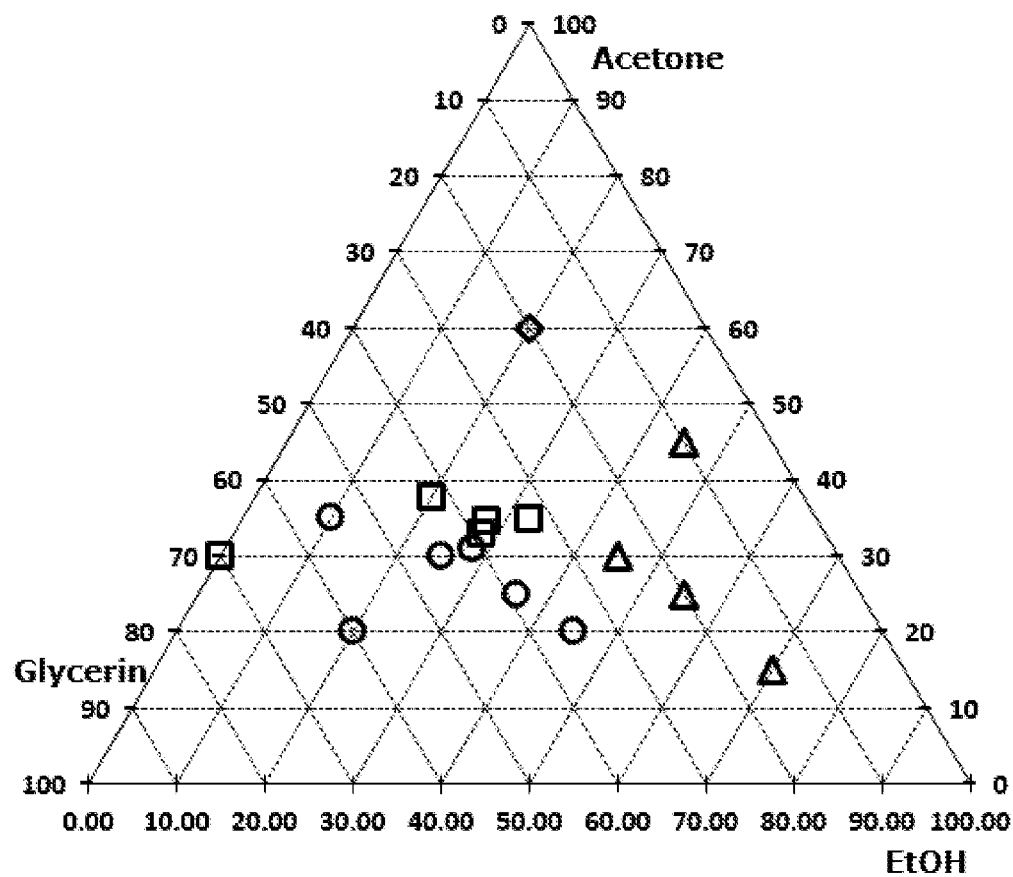
FIG. 1 is a diagram using data developed by the inventors, showing co-mixtures of glycerin, acetone and ethanol, and thickeners used therewith.

As used herein, the expression "at least one" means one or more and thus includes individual components as well as mixtures/combinations. All percentages listed are by weight unless otherwise noted.

Furthermore, all concentrations (and concentration ranges) of glycerin, the C2-C3 monoalcohol, and acetone in this specification may apply to just to the co-mixture (described herein) or, in certain embodiments to the entire composition. For example, unless explicitly stated otherwise when the specification states that glycerin may be present in an amount of about 15% to about 60%, not only does this contemplate that range of glycerin concentration in the co-mixture, but it also contemplates that range of concentration of glycerin in the entire composition.

Numerical ranges are inclusive of endpoints and meant to include all combinations and sub-combinations. For example, from about 5%, 10% or 15% to about 20%, 50% or 60% means about 5% to about 20%, about 5% to about 50%, about 5% to about 60%, about 10% to about 20%, about 10% to about 50%, about 10% to about 60%, about 15% to about 20%, about 15% to about 50%, or about 15% to about 60%.

Other than in the operating examples, or where otherwise indicated, all numbers expressing quantities of ingredients and/or reaction conditions are to be understood as being modified in all instances by the term "about," meaning within 10% of the indicated number, such as within about 5%, such as within 1% or 2% of the indicated number.

"Essentially free" means that the composition includes less than about 3% of the identified ingredient. "Substantially free" means that the composition contains less than about 2% of the identified ingredient. "Free" means that the composition contains less than 1% of the identified ingredient.

"Nail" as used herein includes fingernails as well as toenails.

The compositions, coats and methods of the present invention can comprise, consist of, or consist essentially of the essential elements and limitations of the invention described herein, as well as any additional or optional ingredients, components, or limitations described herein or otherwise useful.

For purposes of the compositions and methods of the present invention where the invention "consists essentially of" the identified ingredients and/or process steps, the two "basic and novel properties" of such compositions and/or methods are "removing nail polish from nails," and "phase stability."

Compositions for Removing Nail Polish

The inventors have found that while glycerin serves as an efficient humectant for moisturizing the skin, glycerin is generally immiscible with acetone and ethyl acetate. However, the inventors have found that certain mixtures of these acetone/alkyl acetate plus C2-C3 monoalcohols and glycerin components along with certain thickeners are indeed capable of being thickened and capable of removing nail polish. The inventors have further surprisingly found that if one desires to thicken such a system, the appropriate choice of thickener depends upon the relative concentrations of glycerin, solvent, and C2-C3 monoalcohol.

Co-Mixture

As described above, compositions of the present invention include a co-mixture that consists of three components: (1) C2-C3 monoalcohol, (2) glycerin, and (3) a solvent selected from the group consisting of acetone, C2-C4 alkyl acetate, and, combinations thereof. While the co-mixture includes no other components than (1), (2), and (3) above, the entire composition may include other components, as described in this specification. Within the composition all C2-C3 monoalcohols, all C2-C4 alkyl acetates (if present) as well as the glycerin and acetone (if present) are considered to be part of the co-mixture. According to certain notable embodiments, the co-mixture exists as a single phase which may or may not include other components.

Glycerin

In accordance with the present invention, compositions for removing nail polish comprising glycerin (a.k.a., glycerol, glycerine, propanetriol, 1,2,3-Trihydroxypropane or 1,2,3-Propanetriol) are provided. By glycerol, it is meant the polyol compound $C_3H_8O_3$, having the general structure below as well as, in certain embodiments, isomers thereof.

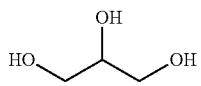

Glycerin may be present in the co-mixtures useful in the present invention in an amount of from about 5%, 10%, 15%, 20%, or 25% by weight to about 45%, 50%, 55%, 70% 80% or 85% by weight. In certain notable embodiments the glycerin is present in a concentration no more than 80%, such as no more than 55% by weight, such as at least about 15%, such as at least about 30%, such as from 15% to 70%, such as from about 30% to about 70% by weight, with all weights being based on the weight of the co-mixture.

C2-C3 Monoalcohol

In accordance with the present invention, compositions for removing nail polish comprising a C2-C3 monoalcohol are provided.

"C2-C3 monoalcohol" means an alcohol having 2 or 3 carbon atoms such as ethanol, propanol, and isopropanol. In certain embodiments the C2-C3 monoalcohol is ethanol.

The C2-C3 monoalcohol is present in the co-mixtures useful in the present invention in an amount of from about 5%, 10%, 15% or 25% by weight to about 25%, 30%, 40%, or 50% by weight. In certain notable embodiments, the C2-C3 monoalcohol is present in the compositions of the present invention in an amount of from about 5% to about 50%, such as from about 15% to about 40% by weight.

Nail-Polish Removing Solvent

In accordance with the present invention, compositions for removing nail polish comprising a nail polish-removing solvent selected from acetone, a C2-C4 alkyl acetate, and combinations (across all relative proportions of acetone and ethyl acetate) thereof. For clarity, the term ""solvent" used herein, is meant to be used only for solvents selected from acetone, a C2-C4 alkyl acetate, and combinations thereof, not for C2-C3 monoalcohols or other constituents that might otherwise be described as "solvents."

According to certain embodiments of the invention, the nail-polish removing solvent is predominantly acetone. "Predominantly" acetone means>50% by weight acetone as a percentage of all solvents selected from acetone and C2-C4 alkyl acetates in the composition. According to certain other embodiments of the invention, the nail-polish removing solvent is predominantly C2-C4 alkyl acetate (defined similarly to above). In certain embodiments, the C2-C4 alkyl acetate is acetone, and in other embodiments, the is C2-C4 alkyl acetate is ethyl acetate.

In yet other embodiments, in order to provide phase compatibility, the compositions are substantially free of alkylene carbonates such as propylene carbonate.

The nail polish-removing solvent may be present in the co-mixtures useful in the present invention in an amount from about 10%, 20%, 25% or 30% to about 40%, 50%, 70% or 85% by weight. In certain notable embodiments, the nail polish-removing solvent is present in a concentration no more than about 50%, such as from about 5% to about 50% (e.g., such as when predominantly or all acetone), such as from about 15% to about 50% (e.g., such as when predominantly or all C2-C4 alkyl acetate), such as no more than 40% such as from about 10% to about 40%. In certain embodiments, the solvent is acetone and the concentration by weight is less than about 50% (e.g., such as when predominantly or all acetone), such as less than about 30% (e.g., such as when predominantly or all C2-C4 alkyl acetate). In other embodiments, the solvent is present in at least 34% by weight, such as from 34% by weight to about 40% by weight. In other embodiments, the solvent is acetone and the concentration by weight is from about 30% to about 40%

Glycerin to Solvent Weight Ratio

Compositions of the present invention have a concentration by weight of water in the composition that is less than the concentration by weight of glycerin. The inventors have found that stable systems that are essentially free of water can be thickened with polyacrylamide. According to this embodiment, such compositions have a co-mixture that has a glycerin to solvent weight ratio (i.e., the concentration by weight of glycerin divided by the concentration by weight of: total acetone and/or C2-C4 alkyl acetate) that is at least about 1.2. In other words, the concentration of glycerin exceeds that of the nail polish removing solvent. For cases in which the nail polish removing solvent is predominantly or (in other embodiments) includes C2-C4 alkyl acetate, the glycerin to solvent weight ratio should be at least about 2.0. In certain other embodiments, in order to optimize nail polish removal, the glycerin to solvent weight ratio should be no more than 3.0, such as no more than about 2.5. For sake of clarity, by "glycerin to solvent weight ratio that are at least about 1.2," it is meant that if, for example, the concentration by weight of glycerin is (about) 48% by weight, then the concentration by weight of the solvent is no more than (about) 40% by weight.

However, in certain other embodiments, the inventors have also found that in order to maintain stability, for compositions that include water, such as about 3% to about 10% water, and are thickened with polyacrylamide, the glycerin to solvent weight ratio may be less than about 2.0. For such cases in which the nail polish removing solvent is predominantly or (in certain embodiments) includes a C2-C4 alkyl acetate, the glycerin to solvent weight ratio should be less than about 1.2. For cases in which the nail polish removing solvent is predominantly or (in certain embodiments) includes acetone, the glycerin to solvent weight ratio should be less than about 1.2.

Glycerin to C2-C3 Monoalcohol Weight Ratio

As discussed, the inventors have further surprisingly identified that sufficiently high levels of glycerin can be beneficially incorporated into thickened compositions including solvents that glycerin is not generally compatible with—acetone/C2-C4 alkyl acetates. Accordingly, co-mixtures useful in the present invention have may ratios by weight of glycerin to C2-C4 monoalcohol that is greater than about 0.6. For sake of clarity, by "ratios by weight of glycerin to C2-C4 monoalcohol that are greater than about 0.6," for example, it is meant that if the concentration by weight of glycerin is (about) 30%, then the concentration by weight of C2-C3 monoalcohol is less than (about) 50% by weight. In certain other embodiments, the ratio by weight of glycerin to C2-C4 monoalcohol that is at least about 0.9 to about 1.4; and the ratio by weight of glycerin to solvent that is at least about 1 to about 1.5.

According to certain notable embodiments of the invention, the C2-C3 monoalcohol is ethanol and the solvent is either acetone or ethyl acetate, or combinations thereof. According to certain other embodiments, the C2-C3 monoalcohol is ethanol and the solvent is acetone.

Polyacrylamide

In accordance with the present invention, compositions for removing nail polish comprising at least one polyacrylamide polymeric thickening agent are provided. Non-limiting examples of thickening agents that may be used according to various embodiments of the present invention include those conventionally used in cosmetics.

"Acrylamide thickening agent" or "acrylamide thickener" as used herein refers to polymers based upon one or more acrylamide monomers or similar monomers.

Specific non-limiting examples of suitable thickening agents include crosslinked anionic copolymers of acrylamide and of AMPS, e.g. in the form of a water-in-oil emulsion, such as those sold under the name SEPIGEL 305 (INCI name: Polyacrylamide/C13-14 Isoparaffin/Laureth-7) and under the name SIMULGEL 600 (CTFA name: Acrylamide/Sodium acryloyldimethyltaurate copolymer/Isohexadecane/Polysorbate 80); and those under the name SEPIPLUS 265 (Acrylamide/ammonium acrylate copolymer/polyisobutene/polysorbate 20), and those under the name SEPIMAX ZEN (ammonium 2-acrylamido 2-methylpropanesulfonate/dimethylacrylamide/hydrophobic chain copolymer, INCI: Polyacrylate Crosspolymer-6), all by SEPPIC. Other examples include those under the name SENSOGEL 200 (INCI: Hydroxyethyl acrylate/Sodium Acryloyl Dimethyl Taurate Copolymer by Applechem, Inc; those under the name Bluevisc AC (INCI: Acrylamide/Sodium acrylate Copolymer) by Blue Sun International; those under the name OPULYN 303B (INCI: Styrene Acrylamide Copolymer) by Univar Solutions; and those under the name Noevender EC-1 (INCI: Acrylates/Acrylamide/Copolymer) by Lubrizol.

The at least one thickening polyacrylamide or cellulose-based agent may be present in the compositions of the present invention in an amount greater than 0.05% by weight, such as greater than 0.1% by weight, such as greater than 0.5% by weight, such as greater than 1% by weight and may be less than 15% by weight, including all ranges and subranges therebetween such as, for example, from about 0.1% to about 15%, such as from about 0.1% to about 10%, such as from about 0.5% to about 10%, such as from about 0.75% to about 7.5%, such as from about 1% to about 5%, etc., with all weights being based on the weight of the composition.

While in certain notable embodiments, the composition is a single phase, in certain other embodiments, the composition may comprise multiple phases.

According to certain other embodiments, the composition may comprise a (e.g., a single) multicomponent solution phase including the co-mixture, and a suspended solid phase that is suspended in the multicomponent solution phase. The suspended solid phase may include any of various ingredients that do not dissolve in the multicomponent solution phase and are capable of being suspended therein. According to certain notable embodiments, the suspended solid phase includes one or more abrasive compounds.

Abrasive Compound

In accordance with the present invention, compositions for removing nail polish comprising at least one abrasive compound (abrasive system) are provided. An "abrasive compound" is a compound capable of providing abrasion or mechanical exfoliation and in accordance with the present invention has one or more of the following characteristics:

(1) Surface roughness: particles with irregular edges provide for abrasion; (2) shape: the particles of the abrasive compound may have a non-angular shape such as a disc, oval or sphere; (3) average particle size: in the context of abrasive compounds from mineral origins, shells, seeds micronized fruit kernel powders, and the like. The particles of the abrasive may have a particle size of 1000 microns (μm) or less, such as 500 μm or less, such as 300 μm or less, such as 150 μm or less, such as 75 μm or less, such as, 50 μm or less such as 30 μm or less; and (4) hardness: the abrasive particles may be soft so as to provide for mild abrasion. According to certain embodiments, the abrasive of the present invention has at least two of the above-mentioned properties, such as at least three of the above-mentioned properties, such as all four of the above-mentioned properties. For example—the abrasive compound may be a large spherical material and not hard; or very small, hard, and having an irregular shape. The hardness may be between (inclusive of endpoints) 3-8 (Mohs hardness); or between 40-60 (Shore D hardness) if the compound is a wax or polymer.

The abrasive of the present invention may have at least two of the above-mentioned properties, such as at least three of the above-mentioned properties, and such as all four of the above-mentioned properties.

Suitable non-limiting examples of abrasive compounds include, but are not limited to, water-soluble abrasives such as sugars; and/or water-insoluble abrasives such as ground fruit kernel or shell powders, materials such as perlite, pumice or apricot kernel, coconut scrubs, zeolites, hydrated silica, calcium carbonate, dicalcium phosphate dihydrate, calcium pyrophosphate, alumina, sodium bicarbonate, polylactic acid, spherical waxes (for example, jojoba scrubeads), as well as synthetic polymeric materials such as polyethylene, polypropylene, polyethylene terephthalate, polymethyl methacrylate or nylon.

The at least one abrasive compound may be present in the compositions of the present invention in an amount greater than 0.5% by weight, such as greater than 1% by weight, such as greater than 2.5% by weight, such as greater than 5% by weight such as less than 40% by weight, including all ranges and subranges therebetween such as, for example, from 0.5% to 40%, such as from 1% to 30%, such as from 2.5% to 25%, such as from 5% to 20%, etc., with all weights being based on the weight of the composition. However, it is to be understood that these weight amounts in this paragraph refer to the total amount of abrasive compound present, including those particles which particles of the abrasive compound used in accordance with the present invention which do not have the smoothness, shape, size and/or surface roughness characteristics discussed above.

The suspended solid phase may include other particulate material such as pigments, optical modifiers, tactile modifiers, and the like.

Compositions of the present invention include water. According to certain embodiments of the present invention, the compositions for removing nail polish have a concentration by weight of water in the composition that is from about 3% to about 10% by weight, such as from about 3% water to about 5% by weight of water.

In certain embodiments of the invention are essentially free, substantially free, or free of oils. As used herein, by "oils," it is meant compounds having a melting point of less than about 30° C. and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the oil does not include hydroxyl moieties.

Suitable examples of compounds of oils include vegetable oils (glyceryl esters of fatty acids, monoglycerides, diglycerides, triglycerides) and fatty esters. Specific non-limiting examples include, without limitation, esters such as isopropyl palmitate, isopropyl myristate, isononyl isonanoate $C_{12}$-$C_{15}$ alkyl benzoates, caprylic/capric triglycerides, ethylhexyl hydroxystearate, silicone oils (such as dimethicone and cyclopentasiloxane), pentaerythritol tetraoctanoate and mineral oil. Other examples of oils include liquid organic ultraviolet filter commonly used for example as UV-absorbing sunscreens such as octocrylene, octyl salicylate, octyl methoxyxcinnamate, among others.

The compositions according to the invention can be manufactured by known processes used generally in the cosmetics or dermatological field.

According to certain embodiments, methods of removing nail polish from nails comprising applying a composition for removing nail polish described above to nails onto which nail polish has been previously applied and removing the nail polish from the nails are provided.

According to certain other embodiments, methods of removing nail polish from nails (and optionally moisturizing hands) include the steps of applying a composition for removing nail polish described above to the hands as well as to the nails onto which nail polish has been previously applied; and removing the nail polish from the nails. The composition may also be rinsed from the hands and nails such as with water. In certain embodiments, compositions of the present invention may be advantageously used without an absorbent pad (otherwise commonly used to remove nail polish from the nails). As a result of the thickened consistency of the inventive compositions, they may also have reduced tendency to spill.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example I(a)—Removability

An experiment was conducted to assess removability of nail polish using sixteen compositions including ethanol, acetone, and glycerin. Sixteen mixtures of ethanol, glycerin, and acetone were prepared by combining the ingredients in the relative concentrations by weight listed below and mixing on high speed vortex for 10 seconds.

Six mm draw down cards were prepared using ESSIE Russian Roulette nail lacquer available from L'Oreal SA of Paris, France. The cards were allowed to dry for 24 hours.

Mixtures were stirred with a spatula, and one spatula scoop of mixture was placed on a cotton pad. The pad was folded in half three times, and the card was wiped until the polish was removed, counting the number of strokes needed. The observation was recorded in Table 1, below:

TABLE 1

Nail Polish Removability for Acetone/Ethanol/Glycerin System

| Ref. | Acetone Conc. | Ethanol Conc. | Glyc. Conc. | Glyc./ Ethanol Ratio | Glyc./ Acetone Ratio | # of Wipes To Remove |
|---|---|---|---|---|---|---|
| A | 60 | 20 | 20 | 1.00 | 0.33 | — |
| B | 20 | 20 | 60 | 3.00 | 3.00 | 100+ |
| C | 30 | 45 | 25 | 0.56 | 0.83 | 10 |
| D | 45 | 45 | 10 | 0.22 | 0.22 | 4 |
| E | 30 | 25 | 45 | 1.80 | 1.50 | 31 |
| F | 34.8 | 32.7 | 32.6 | 1.00 | 0.94 | 8 |
| G | 34.6 | 28.0 | 37.4 | 1.33 | 1.08 | 11 |
| H | 30.9 | 28.1 | 41.0 | 1.46 | 1.33 | 10 |
| I | 37.7 | 20.2 | 42.1 | 2.09 | 1.12 | 18 |
| J | | | | | | |
| K | 25 | 36 | 39 | 1.08 | 1.56 | 27 |
| L | 33 | 28 | 39 | 1.39 | 1.18 | 25 |
| M | 20 | 45 | 35 | 1.57 | 0.285 | 26 |
| N | 20 | 45 | 35 | 0.78 | 1.75 | 25 |
| O | 25 | 55 | 20 | 0.36 | 0.80 | 36 |
| P | 15 | 70 | 15 | 0.21 | 1.00 | 8 |
| Q | 30 | 0 | 70 | — | 2.33 | 18 |

Example I(b)—Removability

An experiment was conducted to assess removability of nail polish, similarly to Example I (a), using seventeen compositions including ethanol, ethyl acetate, and glycerin. The observations were recorded in Table 2, below:

TABLE 2

Nail Polish Removability for Ethyl Acetate/Ethanol/Glycerin System

| Ref. | E Conc. | Ethanol Conc. | Glyc. Conc. | Glyc./ Ethanol Ratio | Glyc./ Acetone Ratio | # of Wipes To Remove |
|---|---|---|---|---|---|---|
| A | 30 | 40 | 30 | 0.75 | 1.00 | — |
| B | 30 | 45 | 25 | 0.55 | 0.83 | 20 |
| C | 30 | 45 | 25 | 1.80 | 1.5 | — |
| D | 40 | 15 | 45 | 3.00 | 1.12 | 100+ |
| E | 25 | 25 | 50 | 2.00 | 2.00 | 22 |
| F | 20 | 35 | 45 | 1.285 | 2.25 | 50 |
| G | 20 | 15 | 65 | 4.33 | 3.25 | 100+ |
| H | 20 | 45 | 35 | 0.78 | 1.33 | 55 |
| I | 20 | 25 | 55 | 2.20 | 2.75 | 27 |
| J | 15 | 30 | 55 | 1.83 | 3.67 | 55 |
| K | 25 | 35 | 40 | 1.14 | 1.60 | 39 |
| L | 30 | 10 | 60 | 6.00 | 2.00 | 100+ |
| M | 25 | 20 | 55 | 2.75 | 2.20 | 45 |
| N | 10 | 40 | 50 | 1.25 | 5.00 | 38 |
| O | 15 | 55 | 30 | 0.54 | 2.00 | 48 |
| P | 55 | 35 | 10 | 0.285 | 0.18 | — |
| Q | 20 | 60 | 20 | 0.33 | 1.00 | — |

Example II(a)—Phase Stability

The sixteen co-mixtures mixtures of ethanol, glycerin, and acetone above were prepared as above (in Example I(a) by combining the ingredients in the relative concentrations by weight listed below and mixing on high speed vortex for 10 seconds.

A first test formulation was prepared for adding sufficient SEPIGEL 305 to the co-mixture to yield 4% by weight SEPIGEL 305 (1.6% active polyacrylamide) and mixed in an attempt to produce a stable thickened composition.

The mixtures were evaluated after one hour and twenty-four hours by visually assessing the thickened appearance/phase stability of the mixtures, looking for visible phase separation or solvent syneresis as an indication of instability. If a stable, thickened composition was produced a "Y" was recorded in the Table 3 below. Otherwise a "N" (no) was recorded.

If the composition was not thickened and phase stable, a second composition was prepared by adding sufficient SEPIGEL 305 to the co-mixture to yield 4% by weight SEPIGEL 305 and adding sufficient water to the co-mixture to yield 4% by weight of water. If a stable, thickened composition was produced a "Y" was recorded in the Table 3 below. Otherwise a "N" (no) was recorded.

If this second composition was not thickened and phase stable, a third composition was prepared by adding sufficient KLUCEL MF PHARM (100% active hydroxypropylcellulose) to the co-mixture to yield 4% by weight of hydroxypropylcellulose. If a stable, thickened composition was produced a "Y" was recorded in the Table 3 below. Otherwise a "N" (no) was recorded.

A first test formulation was prepared for adding sufficient SEPIGEL 305 to the co-mixture to yield 4% by weight SEPIGEL 305 (1.6% active polyacrylamide) and mixed in an attempt to produce a stable thickened composition.

The results are indicated in Table 3, below. If a stable, thickened composition was produced a "Y" was recorded in the Table 3 below. Otherwise a "N" (no) was recorded.

If the composition was not thickened and phase stable, a second composition was prepared by adding sufficient SEPIGEL 305 to the co-mixture to yield 4% by weight SEPIGEL 305 and adding sufficient water to the co-mixture to yield 4% by weight of water. If a stable, thickened composition was produced a "Y" was recorded in the Table 3 below. Otherwise a "N" (no) was recorded. Table 3 also shows concentrations by weight of ethanol, glycerin, and acetone in the co-mixture, as well as glycerin to acetone weight ratio and glycerin to ethanol weight ratio.

TABLE 3

Thickening/Stability for Acetone/Ethanol/Glycerin System

| Ref. | Acetone Conc. | Ethanol Conc. | Glyc. Conc. | Glyc./ Ethanol Ratio | Glyc./ Acetone Ratio | Stable/ Thickened PA, No water (Y/N) | Stable/ Thickened PA, Plus water (Y/N) | Stable/ Thickened Cellulose (Y/N) |
|---|---|---|---|---|---|---|---|---|
| A | 60 | 20 | 20 | 1.00 | 0.33 | N | N | N |
| B | 20 | 20 | 60 | 3.00 | 3.00 | Y | | |
| C | 30 | 45 | 25 | 0.56 | 0.83 | N | Y | |
| D | 45 | 45 | 10 | 0.22 | 0.22 | N | Y | |
| E | 30 | 25 | 45 | 1.80 | 1.50 | Y | | |
| F | 34.8 | 32.7 | 32.6 | 1.00 | 0.94 | N | Y | |
| G | 34.6 | 28.0 | 37.4 | 1.33 | 1.08 | N | Y | |
| H | 30.9 | 28.1 | 41.0 | 1.46 | 1.33 | Y | | |
| I | 37.7 | 20.2 | 42.1 | 2.09 | 1.12 | N | Y | |
| K | 25 | 36 | 39 | 1.08 | 1.56 | Y | | |
| L | 33 | 28 | 39 | 1.39 | 1.18 | N | Y | |
| M | 20 | 45 | 35 | 1.57 | 0.285 | Y | | |
| N | 20 | 45 | 35 | 0.78 | 1.75 | Y | | |
| O | 25 | 55 | 20 | 0.36 | 0.80 | N | N | Y |
| P | 15 | 70 | 15 | 0.21 | 1.00 | N | N | Y |
| Q | 30 | 0 | 70 | — | 2.33 | N | Y | |

The sixteen mixtures of ethanol, glycerin, and ethyl acetate above were prepared as above (in Example 1(b)) by combining the ingredients in the relative concentrations by weight listed below and mixing on high speed vortex for 10 seconds. The mixtures were evaluated after one hour and twenty-four hours by visually assessing the thickened appearance/phase stability of the mixtures, looking for visible phase separation or solvent syneresis as an indication of instability. If a stable, thickened composition was produced a "Y" was recorded in the Table 3 below. Otherwise a "N" (no) was recorded. If a stable, thickened composition was produced a "Y" was recorded in the Table 3 below. Otherwise a "N" (no) was recorded.

If the composition was not thickened and phase stable, a second composition was prepared by adding sufficient SEPI-GEL 305 to the co-mixture to yield 4% by weight SEPIGEL 305 and adding sufficient water to the co-mixture to yield 4% by weight of water. If a stable, thickened composition was produced a "Y" was recorded in the Table 4 below. Otherwise a "N" (no) was recorded. Table 4 also shows concentrations by weight of ethanol, glycerin, and ethyl acetate (EtAc) in the co-mixture, as well as glycerin to ethyl acetate weight ratio and glycerin to ethanol weight ratio.

TABLE 4

Thickening/Stability for Ethyl Acetate (EtAc)/Ethanol/Glycerin System

| Ref. | EtAc Conc. | Ethanol Conc. | Glyc. Conc. | Glyc./ Ethanol Ratio | Glyc./ EtAc Ratio | Stable/ Thickened PA, No water (Y/N) | Stable/ Thickened PA, Plus water (Y/N) |
|---|---|---|---|---|---|---|---|
| A | 30 | 40 | 30 | 0.75 | 1.00 | N | N |
| B | 30 | 45 | 25 | 0.55 | 0.83 | N | Y |
| C | 30 | 45 | 25 | 1.80 | 1.5 | N | N |
| D | 40 | 15 | 45 | 3.00 | 1.12 | N | Y |
| E | 25 | 25 | 50 | 2.00 | 2.00 | Y | |
| F | 20 | 35 | 45 | 1.285 | 2.25 | Y | |
| G | 20 | 15 | 65 | 4.33 | 3.25 | Y | |
| H | 20 | 45 | 35 | 0.78 | 1.33 | N | Y |
| I | 20 | 25 | 55 | 2.20 | 2.75 | Y | |
| J | 15 | 30 | 55 | 1.83 | 3.67 | Y | |
| K | 25 | 35 | 40 | 1.14 | 1.60 | N | N |
| L | 30 | 10 | 60 | 6.00 | 2.00 | N | N |
| M | 25 | 20 | 55 | 2.75 | 2.20 | Y | |
| N | 10 | 40 | 50 | 1.25 | 5.00 | Y | |
| O | 15 | 55 | 30 | 0.54 | 2.00 | N | Y |
| P | 55 | 35 | 10 | 0.285 | 0.18 | N | N |
| Q | 20 | 60 | 20 | 0.33 | 1.00 | N | N |

Figure 2:
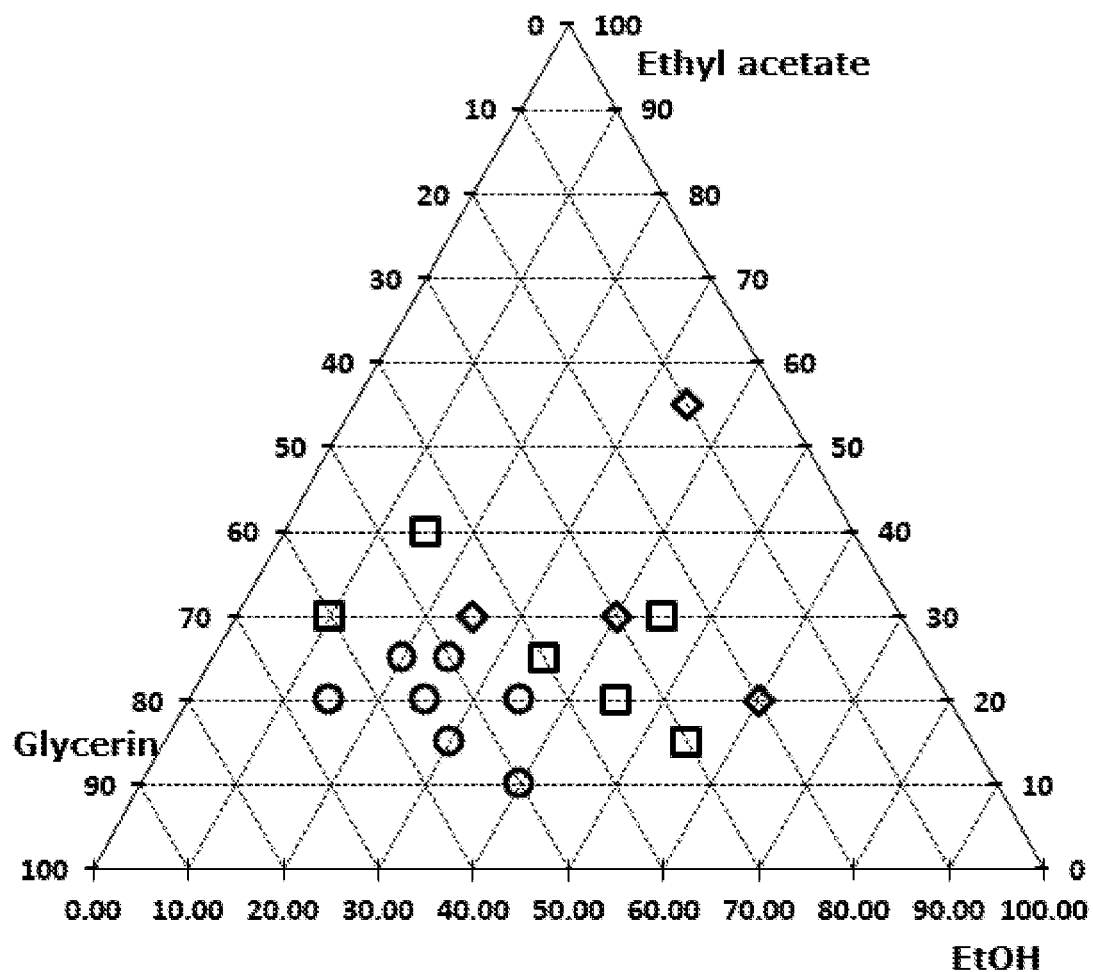
FIG. 2 is a diagram using data developed by the inventors, showing co-mixtures of glycerin, ethyl acetate and ethanol, and thickeners used therewith.

The results are further displayed in FIG. 1 (acetone) and FIG. 2 (ethyl acetate), which are essentially diagrams depicting the results of thickening/stability testing for particular compositions. Circles indicate compositions which were successfully thickened with polyacrylamide (no added water). Squares indicate compositions that were successfully thickened with polyacrylamide with 4% added water but were not successfully thickened with polyacrylamide with no added. Furthermore, for FIG. 1, triangles indicate compositions which were successfully thickened with cellulose polymer but were not successfully thickened with polyacrylamide (either with no added or with added water). Diamonds indicate compositions that were not successfully thickened with polyacrylamide, nor with polyacrylamide with added water, nor with cellulose polymer.

The removability and phase stability results for the acetone system indicate that if one desires to include about 15% or more of glycerin, one should use up to about 65% by weight of ethanol, about 15% to about 60% by weight of glycerin, and about 20% to about 85% acetone to achieve high removability. To work with a single phase system one would use about 10% to about 65% ethanol, whereas to work with a two phase system, one would use 0% to about 10% ethanol.

While the removability data for ethyl acetate is unreliable, the phase stability results for the ethyl acetate system show that if one desires to include about 15% or more of glycerin, then it may be desirable for the composition to include from about 25% up to about 75% by weight of a C2-C3 monoalcohol, about 15% to about 70% by weight of glycerin, and about 10% to about 60% by weight of C2-C4 alkyl acetate.

What is claimed is:

1. A composition for removing nail polish comprising:
   a co-mixture that consists of:
      C2-C3 monoalcohol;
      glycerin; and
      less than about 50% by weight with respect to the weight of the co-mixture of nail polish-removing solvent selected from the group consisting of acetone, C2-C4 alkyl acetate(s), and mixtures thereof,
   wherein acetone is either not present in the composition or, if present, it is present in an amount such that the composition is essentially free of acetone, and
   wherein the glycerin and the C2-C3 monoalcohol are present in a glycerin to C2-C3 monoalcohol weight ratio of greater than about 0.6,
   polyacrylamide, and
   water,
   wherein the concentration by weight of water in the composition is
   less than the concentration by weight of glycerin.

2. The composition of claim 1, wherein the concentration by weight of water in the composition is from about 3% to about 10% by weight.

3. The composition of claim 1, wherein the concentration by weight of water in the composition is from about 3% to less than 5% by weight.

4. The composition of claim 1, wherein the glycerin and C2-C4 alkyl acetate are present in a glycerin to C2-C4 alkyl acetate weight ratio less than about 2.0.

5. The composition of claim 1, wherein the concentration of C2-C4 alkyl acetate in the co-mixture is no more than 40% by weight with respect to the weight of the co-mixture.

6. The composition of claim 1, wherein the concentration of C2-C4 alkyl acetate in the co-mixture is no more than 30% by weight with respect to the weight of the co-mixture.

7. The composition of claim 1, further comprising suspended solid phase that includes one or more abrasive compounds.

8. The composition of claim 1, further comprising suspended solid phase that includes one or more water-soluble abrasive compounds.

9. The composition of claim 1, wherein the polyacrylamide is present in a concentration by weight from about 0.75% to 7.5% by weight of the composition.

10. The composition of claim 1, wherein the C2-C3 monoalcohol is ethanol.

11. The composition of claim 1, wherein the C2-C3 monoalcohol is ethanol, and wherein the glycerin and the C2-C4 alkyl acetate are present in a glycerin to C2-C4 alkyl acetate weight ratio of less than about 1.2.

12. The composition of claim 1, wherein the C2-C3 monoalcohol is ethanol, and wherein the glycerin and the C2-C4 alkyl acetate are present in a glycerin to C2-C4 alkyl acetate weight ratio of less than about 1.2, and wherein the concentration of C2-C4 alkyl acetate in the co-mixture is no more than 40% by weight with respect to the weight of the co-mixture.

13. A method of removing nail polish from nails and moisturizing the hands of a subject, comprising:

applying a composition to hands and to nails of a subject onto which the nail polish had been previously applied, wherein the composition comprises:

a co-mixture that consists of:

C2-C3 monoalcohol;

glycerin; and less than about 50% by weight with respect to the weight of the co-mixture of nail polish-removing solvent selected from the group consisting of acetone, C2-C4 alkyl acetate(s), and mixtures thereof, wherein acetone is either not present in the composition or, if present, it is present in an amount such that the composition is essentially free of acetone, and wherein the glycerin and the C2-C3 monoalcohol are present in a glycerin to C2-C3 monoalcohol weight ratio of greater than about 0.6, polyacrylamide, and water, wherein the concentration by weight of water in the composition is less than the concentration by weight of glycerin; and removing the nail polish from the nails.

14. The method of claim 13, wherein the concentration by weight of water in the composition is from about 3% to about 10% by weight.

15. The method of claim 13, wherein the concentration of C2-C4 alkyl acetate in the co-mixture is no more than 40% by weight with respect to the weight of the co-mixture.

16. The method of claim 13, wherein the C2-C3 monoalcohol is ethanol, and wherein the glycerin and the C2-C4 alkyl acetate are present in a glycerin to C2-C4 alkyl acetate weight ratio of less than about 1.2, and wherein the concentration of C2-C4 alkyl acetate in the co-mixture is no more than 40% by weight with respect to the weight of the co-mixture.

17. The composition of claim 1, wherein the composition is free of acetone.

* * * * *